(12) United States Patent
Tassignon

(10) Patent No.: US 6,200,342 B1
(45) Date of Patent: Mar. 13, 2001

(54) INTRAOCULAR LENS WITH ACCOMMODATIVE PROPERTIES

(76) Inventor: Marie-Jose B. Tassignon, Wapenhaghestraat, 6, Berchem, 2600 (BE)

( * ) Notice: Subject to any disclaimer, the term of this patent is extended or adjusted under 35 U.S.C. 154(b) by 0 days.

(21) Appl. No.: 09/309,611

(22) Filed: May 11, 1999

(51) Int. Cl.$^7$ ....................................................... A61F 2/16
(52) U.S. Cl. ............................................................ 623/6.37
(58) Field of Search .................................. 623/6.18, 6.19, 623/6.31, 6.22, 6.37–6.39, 6.43, 6.46, 6.47, 635, 6.55, 6.49

(56) References Cited

U.S. PATENT DOCUMENTS

| | | |
|---|---|---|
| 4,759,762 | 7/1988 | Grendahl . |
| 4,892,543 | 1/1990 | Turley . |
| 4,932,966 | 6/1990 | Christie et al. . |
| 5,489,302 | 2/1996 | Skottun . |
| 5,697,973 | 12/1997 | Peyman et al. . |
| 5,725,575 | 3/1998 | O'Donnell . |
| 5,728,155 | 3/1998 | Anello et al. . |
| 5,843,188 | 12/1998 | McDonald et al. . |
| 5,877,839 | 3/1999 | Portney . |

Primary Examiner—David H. Willse

(57) ABSTRACT

A new lens design and method of implantation uses the change in pupil diameter of the eye concurrent with the changes induced by a contraction of the ciliary muscle during the accommodative reflex, in order to assist in focusing of nearby objects. This new intraocular lens consists of two parts. The posterior part or haptic part is inserted behind the iris and in front of the natural lens or artificial implant. Its main purpose is to participate in the accommodative mechanism and to prevent excessive lateral movement and luxation of the lens. An anterior or optical part is made of flexible material and is placed before the iris. Its diameter is variable but should be large enough to cover the pupillary margins to some degree under various conditions of natural dilation. The anterior and posterior part of the lens are separated by a compressible circular groove in which the iris will settle. The diameter of this groove is slightly larger than the pupillary diameter measured under normal photopic daylight conditions and for distance vision. Since the pupil becomes smaller in near vision, the iris will exert a slight pressure at the level of the groove of the lens which will cause a progressive and evenly distributed flexing of the anterior part of the intraocular lens, as the diameter of the compressible circular groove slightly decreases. This flexing will induce an increase in refractive power which corresponds to a variable part of the amount necessary for focusing nearby objects.

8 Claims, 3 Drawing Sheets

Fig. 3A
Fig. 3B
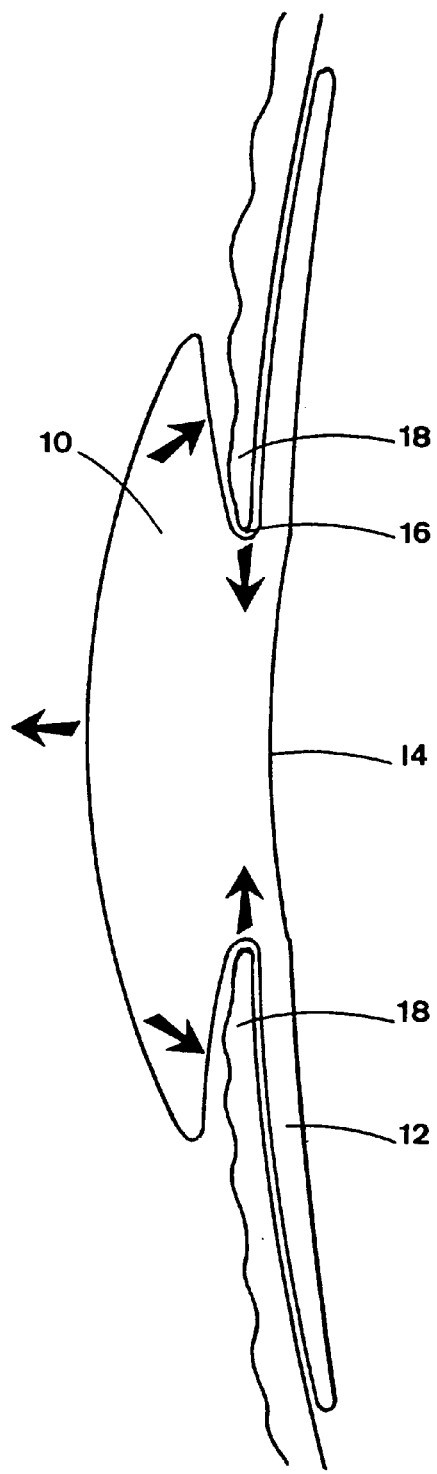
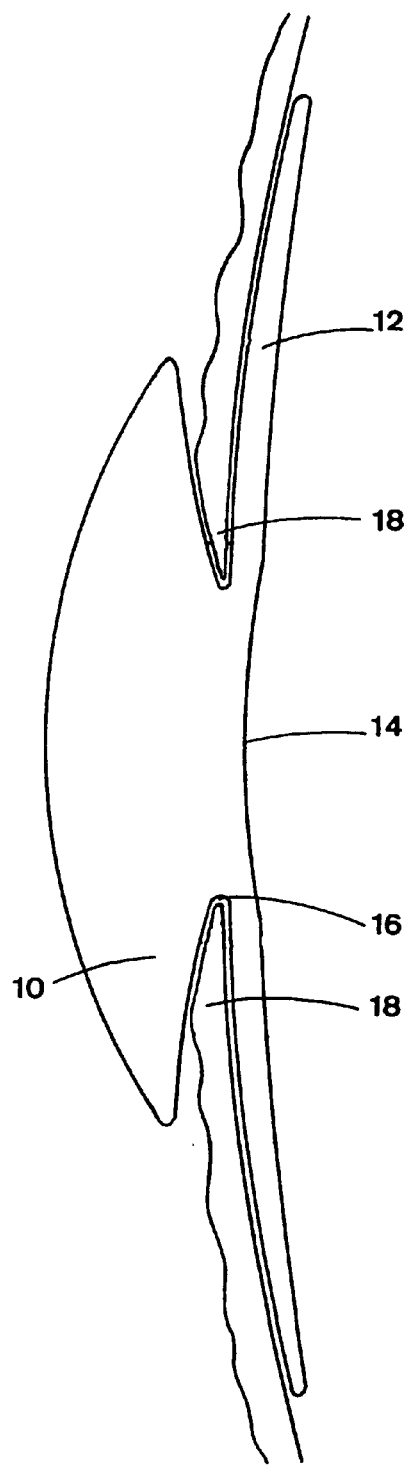

INTRAOCULAR LENS WITH ACCOMMODATIVE PROPERTIES

BACKGROUND—FIELD OF INVENTION

This invention relates to intraocular lenses for implantation in the human eye, in particular intraocular lenses having in vivo accommodative properties to assist or replace part of the focusing capabilities of the eye.

BACKGROUND—DESCRIPTION OF PRIOR ART

The insertion of an intraocular lens in the human eye to correct a refractive error is a well-known surgical procedure. In this procedure, the natural lens may or may not be removed. Several types of intraocular lenses are currently available for this purpose. It is possible to change the optical properties of some of these lenses in vivo, as exemplified in U.S. Pat. No. 5,728,155 awarded to Anello et al. and U.S. Pat. No. 5,725,575 awarded to O'Donnell. These lenses allow a one-time adjustment or finetuning of focusing properties after implantation. Continuous adjustment of focusing range in vivo is not possible. Of particular interest are lenses placed in the anterior chamber of the eye for the correction of high myopia, and the lenses that have multiple optical zones to allow focusing at various distances from the eye. Examples are U.S. Pat. No. 4,759,762 awarded to Grendahl, and U.S. Pat. No. 5,877,839 awarded to Portney. The latter group is primarily intended to correct a condition called presbyopia. In presbyopia, the natural capability of the human lens to change its shape and therefore refractive power, is gradually lost with age. All of the cited prior art artificial lenses however cannot change shape to adjust refractive power on a continuous basis and some may suffer from multiple image formation or blur because of the different active optical areas of the lens that are needed to focus at different distances.

Another lens of interest is documented in U.S. Pat. No. 5,697,973, awarded to Peyman et al. This multipurpose lens can be held in place by the margins of the pupil. However this lens is conceived to avoid changes in its shape.

In ocular physiology, it is well-known that during the accommodative process, a certain amount of iris constriction occurs at the same time of contraction of the ciliary body and medial extraocular rectus muscles. This accomodative mechanism is of a reflex nature, and is self-adjusting within certain limits. Its purpose is to increase the convex posterior curvature of the natural lens by gradually loosening the suspension fibers of the lens. The suspension fibers of the lens relax when certain muscular fibers of the ciliary body contract. This accommodative process fails when the natural lens stiffens with age or is replaced with an artificial lens.

To minic more accurately this physiologic process, lenses have been constructed that respond to anatomical variations of the ciliary body. Several means have been employed. Examples are U.S. Pat. No. 5,843,188 to McDonald et al., U.S. Pat. No. 4,892,543 to Turley, U.S. Pat. No. 5,489,302 to Skottun, and U.S. Pat. No. 4,932,966 to Christie et al. However, these lenses seem to have very little or no accomodative effect. This is probably due to the simultaneous contraction of the iris which pushes the lens posteriorly, thereby neutralizing the forward movements of the lens caused by a contraction of the ciliary muscle. None of the aforementioned lenses can accommodate or change shape, based on a change in diameter of the pupil during the process of accommodative focusing of the eye.

Summary, Object and Advantages of the Invention

The primary purpose of the new lens design and method of implantation is therefore to make use of all the natural mechanisms involved in the accommodative reflex: the change in pupil diameter of the eye and the changes in state of contraction of the ciliary muscle, in order to assist in focusing of nearby objects.

In summary, the new intraocular lens consists of two parts. The posterior part or haptic part is to be inserted behind the iris and in front of the natural lens or artificial implant. The overall length and structure of this part is variable and should fit as close as possible into the ciliary sulcus for two reasons. First, to be able to respond to changes in the state of contraction of the ciliary body and second, to prevent excessive lateral movement and luxation of the lens. An anterior or optical part, made of flexible material, is placed before the iris. Its diameter is variable but should be large enough to cover the pupillary margins to some degree under various conditions of natural dilation. This is important for optical reasons as well as mechanical reasons, to avoid luxation of the optical part behind the iris. The anterior and posterior part of the lens are separated by a compressible circular groove in which the iris will settle. The diameter of this groove is important and must be slightly larger than the pupillary diameter measured under normal photopic daylight conditions and for distance vision. Since the pupil becomes smaller in near vision, the iris will exert a slight pressure at the level of the groove of the lens which will cause a progressive and evenly distributed flexing of the anterior part of the intraocular lens, as the diameter of the compressible circular groove slightly decreases. This flexing will induce an increase in refractive power which basically corresponds to a variable part of the amount necessary for focusing nearby objects.

The use of the change in pupil diameter versus other methods, mentioned in the prior art, is advantageous for several reasons. First, it is easy to observe dynarnically, before the intervention, the change of the pupil diameter under various conditions of background illumination and distances of focusing. Second, during the operation, the intervention is under maximal visual control of the surgeon since no critical steps of the intervention have to take place behind the iris. Lastly, the post-operative status and functioning of the implant is easily observed using the biomicroscope.

Furthermore, this new lens design will avoid the disadvantages of the anterior chamber angle fixation phakic lenses. Because no parts of the new lens will touch the anterior chamber angle, secondary glaucoma and pain will not occur. Because this new lens is located at a safe distance from the corneal endothelium and has no chance to luxate anteriorly because of its attachment to the posterior part of the lens, there is no risk for endothelial touch and subsequent endothelial cell loss. Because this new lens respects the shape and the centration or decentration of the pupillary border, no pupillary deformation will occur.

Also, this new lens design will avoid the disadvantages of the iris fixated anterior chamber phakic lenses. Because this new lens design has no fixed iris fixation but a groove which accommodates the iris in a flexible way, no iris perforation nor pupillary deformation can occur. Because this new lens is covering completely the pupillary margins, no complaints of halos due to decentration are to be expected. Because of its large distance from the corneal endothelium, no corneal touch is possible.

At last, this new lens design will avoid the disadvantages of posterior chamber phakic lenses that solely rely on stabilization by the ciliary body. Because the lens has primarily an iris suspension and streamlined design, lenticular touch and irritation of the ciliary body will be minimized.

Further objects and advantages will be clear from the ensuing description of a preferred embodiment and the accompanying drawings.

DESCRIPTION OF THE DRAWINGS

Features and advantages of the new lens will appear from the following description of preferred embodiments of the invention taken together with the drawings, in which:

FIG. 3A is a side view of the intraocular lens when the sphincter muscle of the pupil is in a resting natural position in the groove, corresponding to far distance focusing under dayight conditions.

FIG. 3B is a side view of the intraocular lens when the sphincter of the pupil is in a contracted state. The anterior part of the intraocular lens is pushed slightly foreward and flexes, as illustrated by the different arrows.

REFERENCE NUMERALS IN DRAWINGS

Figure 1A:
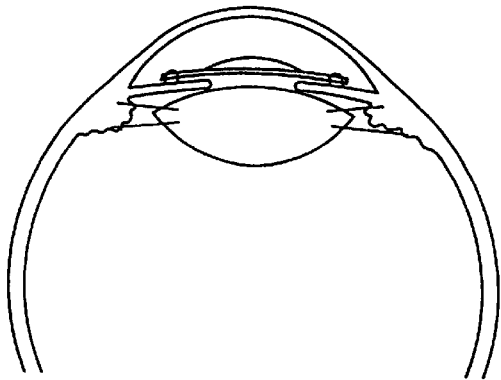
FIG. 1A is an anatomical sectioning through the anterior segment of the eye, illustrating the prior art positioning of a conventional iris supported intraocular lens.
Figure 1B:
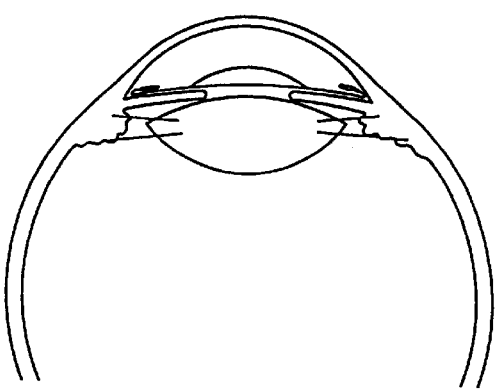
FIG. 1B is an anatomical sectioning through the anterior segment of the eye, illustrating the positioning of a prior art conventional angle supported intraocular lens.
Figure 1D:
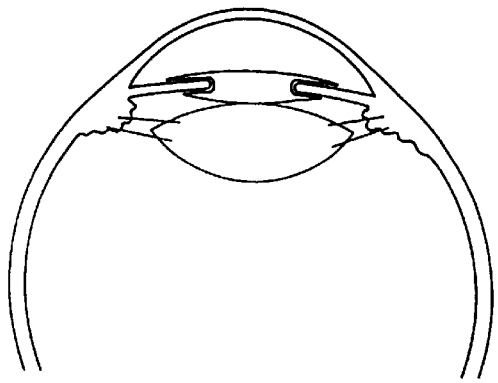
FIG. 1D is an anatomical sectioning through the anterior segment of the eye, illustrating the prior art positioning of a conventional iris suspended intraocular lens.
Figure 1C:
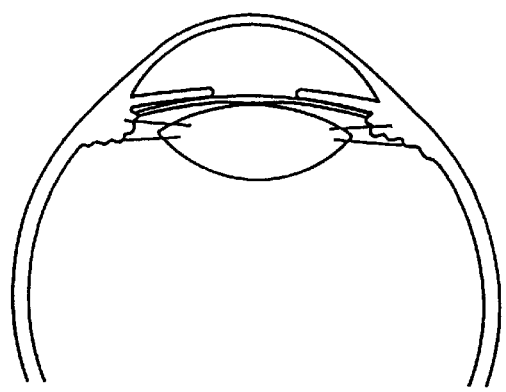
FIG. 1C is an anatomical sectioning through the anterior segment of the eye, illustrating the prior art positioning of a conventional sulcular supported intraocular lens.
Figure 1E:
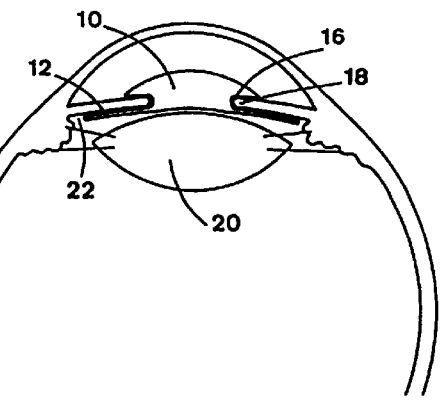
FIG. 1E is an anatomical sectioning through the anterior segment of the eye, illustrating the positioning of the new intraocular lens. The posterior part of the lens is inserted behind the iris and before the natural lens. The anterior part of the lens is located before the iris. The iris is located within the circular groove.

10 Anterior and optical part of the intraocular lens

12 Posterior and haptic part of the intraocular lens

14 Slight anterior vaulting of the posterior part of the intraocular lens

16 Compressible groove, separating the anterior and the posterior part of the intraocular lens 18 Pupil margins with sphincter of the iris, inserted in the groove of the intraocular lens 20 Natural lens or implant 22 Sulcus, delineated by the ciliary body of the eye, in which the posterior haptic part is stabilized

DESCRIPTION OF PREFERRED EMBODIMENTS

FIGS. 1A, 1B, 1C and 1E illustrate the differences in positioning of the new lens in the eye versus the cited prior art. With the new lens design, the anterior optical part is placed before the iris, the pupil margin that contains the sphincter muscle of the iris is inserted in the circular and compressible groove, and the posterior haptic part is placed behind the iris and before the natural lens in the sulcus delineated by the ciliary body and iris. This new streamlined lens design, according to FIG. 1E, permits a more physiologic centration within the pupil and offers the advantages previously mentioned.

Figure 2A:
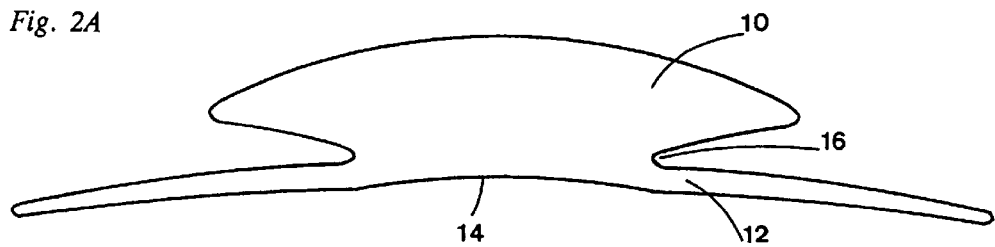
FIG. 2A is a side view of the intraocular lens, showing the groove which accommodates the pupil margins of the iris, the anterior optical part of the intraocular lens which is placed before the iris and the posterior haptic part of the intraocular lens which is placed behind the iris and before the natural lens.
Figure 2B:
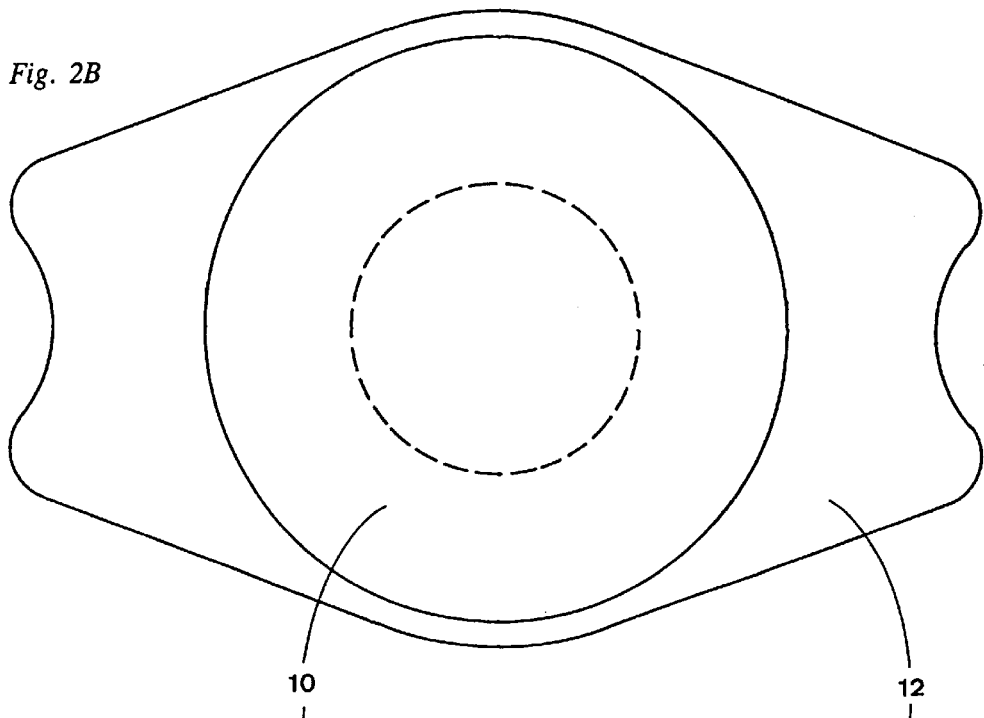
FIG. 2B is a view from above of the intraocular lens, illustrating the anterior optical part which is smaller than the posterior haptic part and is centered on the posterior part.
Figure 2C:
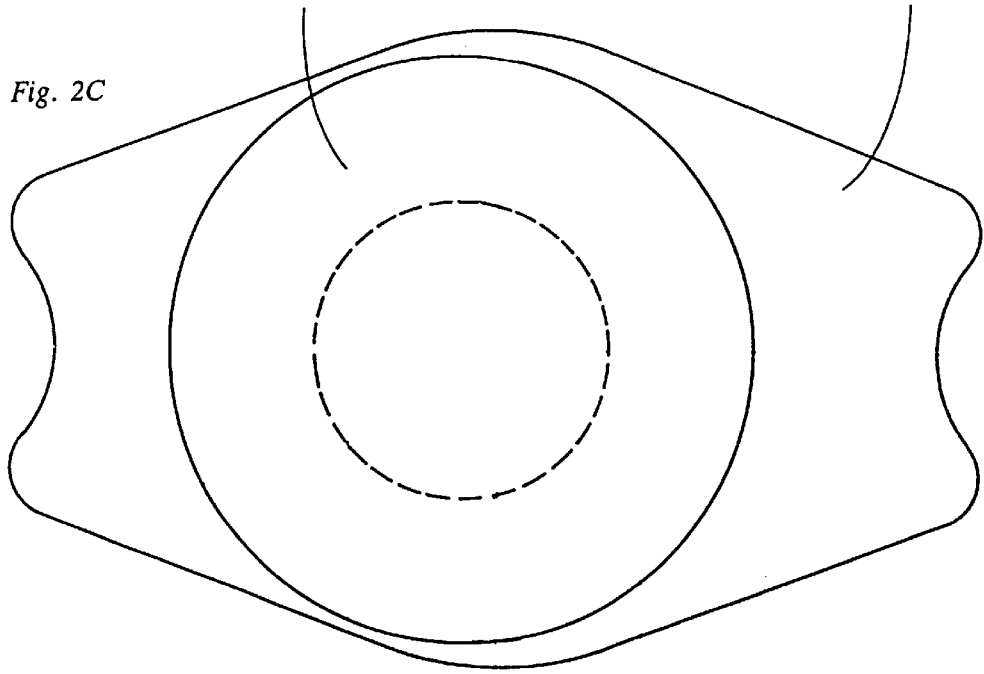
FIG. 2C is a different embodiment of the intraocular lens, illustrating a decentered anterior optical part. This type of intraocular lens is meant to be used in case of a nasally decentered pupillary area.

The preferred embodiment of the optical part 10 of the intraocular lens is circular and its anterior surface is convex, although other configurations and shapes may be employed. The optical part 10 of the intraocular lens may be constructed of any of the currently used deformable substances such as silicone polymeric materials, acrylic polymeric materials, hydrogel forming polymeric materials and mixtures of these materials or alike. The lens materials used can be coated or doped with chemicals for various purposes, as described in prior art. The diameter of the optical part can be variable but preferably should not be less than the average diameter of the pupil as measured under dark background conditions. This will reduce as much as possible the risk of luxation of the optical part behind a contracting iris and will further prevent light reaching the back of the eye without focusing through the optical part, the latter phenomenon causing a blurring sensation or glare. Inadvertant luxation however can nearly always be corrected with positioning of the subject and a medically induced constriction of the pupil. If the anatomical pupil is decentered, e.g. nasally with regard to the iris, a decentered anterior optical part as illustrated in FIG. 2C is useful.

The preferred embodiment of the haptic part 12 is as thin as possible. It follows the general contours of the anterior surface of a human lens and is oval in shape with an overall length which is variable and adjusted to match the surgical <white to white corneal diameter>>.

This is done to obtain the aforementioned optimal stabilization of the lens by the sulcus 22 of the eye and to adapt to the contour of the anterior surface of the lens. The oval shape is purely illustrative and any other configuration may be used, as long as a stable positioning of the intraocular lens is provided. The posterior surface of the haptical part preferably has an anterior vaulting 14 facing the natural lens to promote the circulation of intraocular fluids and to prevent a permanent adherence. The haptic part 12 is preferably made of one piece together with the optical part 10 of the intraocular lens. It can however be affixed to the optical part 10 if this is more convenient for production purposes. The haptic part 12 may be constructed from any of the commonly employed materials as previously described, as well as from more rigid but still flexible material such as polymethyl-metacrylate derivatives.

The circular and compressible groove 16 in the intraocular lens is delineated by the optical part 10 and the haptic part 12. It can be of variable width, depth and shape in order to capture the margins of the iris. A typical groove will taper from 1 mm. to 0.2 mm. Various diameters of the groove 16 are provided to correspond to various pupillary diameters. The preferred diameter to be used in a particular eye, will be slightly larger than the pupillary diameter measured under daylight conditions of illumination and for focusing at a distance. This diameter is choosen to maximize the chances that, upon constriction of the sphincter of the iris during the accomodation reflex, the anterior surface of the optical part becomes more convex. This change in shape provides part or all of the additional dioptric power necessary for near focusing.

Description of a Preferred Surgical Procedure

Prior to surgery, the following variable parameters of the lens have to determined for each patient:

A. The diameter of the posterior haptic part is based on the <white to white diameter>>of the cornea.
B. The diameter of the groove will be derived from the measurement of the pupillary diameter in normal daylight and distance vision, using a computer assisted pupillometer.
C. The diameter of the anterior part of the lens will be based on the diameter of the pupil measured in the dark, using a computer assisted infra-red pupillometer.
D. Pupillary decentration will be determined using anterior segment photographs.
E. The refractive power of the intraocular lens will be determined according to well-known parameters such as the refractive index of the material used, curvature of the anterior surface of the optical part, and biometric data from the eye receiving the intraocular lens.

Once the parameters of the lens are calculated, the surgery can be performed according to the following preferred procedure.

After proper anesthesia has been administered, the eye is opened with a corneal or limbal incision. The length of the opening will depend on the foldability of the intraocular lens. The anterior chamber is partially filled with viscoelastic material while the iris is gently dilated and separated from the natural lens during the same manoeuver. The intraocular lens is then introduced in the anterior chamber of the eye with the optional help of a folder. The posterior part of the lens is placed behind the iris and before the natural lens. The iris in inserted in the groove so that the anterior part of the lens is positioned before the iris. To ensure a good positioning of the lens a drug that constricts the pupil can be injected in the anterior chamber of the eye at this stage of the sugery. In order to prevent a pupillary block type of glaucoma, an iridectomy can be performed prior to surgery with the Q-switched Nd-YAG laser. This can also be done during surgery using specific micro-surgical instruments for this purpose. After removal of the viscoelastic material, the incision of the eye is closed.

Although the above description of the new lens and its method of insertion contain many specifications, these should not be considered as limiting the scope of the invention but as merely providing illustrations of some of the presently preferred embodiments of the invention. Other embodiments of the invention, including additions, subtractions, deletions or modifications of the disclosed embodiments will be obvious to those skilled in the art and are within the scope of the following claims and their legal equivalent.

I claim:

1. An intraocular lens for implantation in the human eye comprising the elements of:
   A. an anterior optical part constructed of a flexible substance and having an anterior surface capable of refracting light;
   B. a posterior haptic part comprising support means, said support means having extensions for positioning in the sulcus of said eye;
   C. a compressible groove, separating said anterior optical part and said posterior haptic part, said compressible groove accomodating the pupil margin of the iris of said human eye;
   whereby a constriction of said pupil during the process of accomodation of said eye will compress said groove to a variable degree, and thereby cause a change in said anterior surface of said anterior optical part.

2. An intraocular lens for implantation in the human eye according to claim 1 wherein said optical part is coated or doped.

3. An intraocular lens for implantation in the human eye according to claim 1 wherein said optical part and said haptic part are of different substances selected from the group containing rigid and deformable biomaterials.

4. An intraocular lens for implantation in the human eye according to claim 1 wherein a diameter of said anterior optical part is larger than the average diameter of said pupil of said eye in darkness.

5. An intraocular lens for implantation in the human eye according to claim 1 wherein the largest diameter of said support means approximates the white to white corneal distance of said eye.

6. An intraocular lens for implantation in the human eye according to claim 1 wherein a diameter of said groove approximates the average diameter of said pupil of said eye in daylight.

7. An intraocular lens for implantation in the human eye according to claim 1 wherein said anterior optical part is decentered with regard to said posterior haptic part.

8. A method for correcting a decreased capability for refracting light in the human eye comprising the steps of permanently positioning an intraocular lens in said eye so that a flexible optical part of said intraocular lens is placed before the iris of said eye, a haptic part of said intraocular lens is placed behind said iris, and the pupil margin of said iris is situated within a compressible groove separating said flexible part and said haptic part of said intraocular lens, and further having said groove of said intraocular lens compressed to a variable degree with said pupil margin of said iris whereby said compression results in an increased capability for refracting light passing through said flexible optical part.

* * * * *